| United States Patent [19] | [11] Patent Number: 4,885,378 |
| Band et al. | [45] Date of Patent: Dec. 5, 1989 |

[54] PREPARATION OF HEXAALKYLCYCLOTRISILTHIANE

[75] Inventors: Elliot I. Band, North Tarrytown, N.Y.; Suzanne T. Eberhart, New Haven, Conn.

[73] Assignee: Akzo America Inc., New York, N.Y.

[21] Appl. No.: 347,309

[22] Filed: May 4, 1989

[51] Int. Cl.$^4$ .............................................. C07F 7/08
[52] U.S. Cl. .................................................. 556/426
[58] Field of Search ........................................ 556/426

[56] References Cited

U.S. PATENT DOCUMENTS 2,567,724  9/1951  Moody .................................. 556/426
3,344,161  9/1967  Moedritzer et al. ................ 556/426
3,506,699  4/1970  Viventi ................................ 556/426

OTHER PUBLICATIONS

Wieber et al., "Berichte", 96, 1963, pp. 1019–1021.
Giolando et al., "Inorg. Chem.", 26, No. 19, 1987, pp. 3080–3082.

*Primary Examiner*—Paul F. Shaver
*Attorney, Agent, or Firm*—Richard P. Fennelly; Louis A. Morris

[57] ABSTRACT

Hexaalkylcyclotrisilthiane compounds (e.g., hexamethylcyclotrisilthiane) are synthesized by reaction of lithium disulfide and a dihalodialkylsilane (e.g., dichlorodimethylsilane) in a non-oxygenated solvent (e.g., acetonitrile).

7 Claims, No Drawings

PREPARATION OF HEXAALKYLCYCLOTRISILTHIANE

BACKGROUND OF THE INVENTION

1. Field of the Invention

The present invention relates to a novel process for the preparation of hexaalkylcyclotrisilthiane.

2. Description of the Prior Art

Hexaalkylcyclotrisilthianes (e.g., hexamethylcyclotrisilthiane) are currently of interest in regard to use as solid electrolytes for rechargeable batteries. Improved processes for the manufacture of such compounds is an area of active interest.

U.S. Pat. No. 2,567,724 teaches that such compounds can be synthesized by reacting an organohalosilane with hydrogen sulfide in the presence of a hydrohalide acceptor(pyridine).

D. M. Giolando et al., in Inorg. Chem. 1987, 26, 3080–3082 discuss the reactivity of metal complexes of dimethylsilanedithiolate. This article mentions (on page 3081) the treatment of tetrahydrofuran solutions of dichlorodimethylsilane with dilithium sulfide followed by treatment with $(MeCp)_2TiCl_2$. They postulate that "the known" hexamethylcyclotrisilthiane "may be" an intermediate in such a synthesis but such a possible intermediate was not proven to have been produced or recovered from the reaction mixture which includes the oxygenated solvent, tetrahydrofuran.

SUMMARY OF THE INVENTION

The present invention relates to the production and isolation of hexaalkylcyclotrisilthiane formed by the reaction of lithium sulfide and dihalodialkylsilane in a non-oxygenated solvent. The absence of an oxygenated solvent is an advantage when the hexaalkylcyclotrisilthiane product is used to prepare titanium disulfide (e.g., by the low temperature route from titanium tetrachloride as described by A. Bensalem et al., Mat. Res. Bull., 23, pp. 857–868 (1988). In a nonoxygenated solvent, the product silane can be used without isolation from the solvent. Oxygenated solvents might cause oxygen contamination problems in the final titanium disulfide, if the product is used to make such a product, due to titanium's strong affinity for oxygen.

DETAILED DESCRIPTION OF THE INVENTION

The hexaalkylcyclotrisilthiane compounds produced by the instant process have the formula

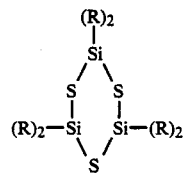

The reaction between the chosen silane reactant and dilithium sulfide can take place using molar ratios of the latter to the former of from about 2:1 to about 10:1 at temperatures ranging from about 20° C. to about 100° C. A molar ratio of about 1:1 is preferred. The solvent medium for the reaction is a non-oxygenated solvent including the aliphatic and aromatic hydrocarbons and their derivatives (e.g., the halogenated and cyano derivatives). Acetonitrile, a highly polar solvent having a high dielectric constant, is a preferred example.

The synthetic conditions used are relatively mild and the yield of product is good.

The following Example further illustrates the invention.

EXAMPLE 1

This Example describes the preparation of hexamethyldisilthiane.

To a dry, nitrogen purged 100 ml flask containing a stir bar, 4.70 grams, 102 mmol, of commercial $Li_2S$ was added, followed by about 15 grams of dry acetonitrile. Then 13.7 grams, 106 mmol, of dichlorodimethylsilane was added by syringe. The vessel was stirred at room temperature for sixty hours and monitored by nmr spectroscopy. The nmr spectra showed the starting silane disappeared and was replaced by resonances at sigma= $-1.27$ ppm and $-1.47$ ppm vs. acetonitrile consistent with $[(CH_3)_2SiSl]_x$ present as a mixture of dimer and trimer. By integration, the reaction yield was 90% with 10% unreacted dichlorodimethylsilane. The product solution was separated from LiCl by filtration.

The foregoing Examples are presented for illustrative purposes and should not therefore be construed in a limiting sense. The scope of protection which is sought is set forth in the claims which follow.

We claim:

1. A process for preparing and recovering a hexaalkylcyclotrisilthiane which comprises the reaction of dilithium sulfide and a dihalodialkylsilane in a non-oxygenated solvent and recovering the hexaalkylcyclotrisilthiane.

2. A process as claimed in claim 1 wherein the dihalodialkylsilane is dichlorodimethylsilane.

3. A process as claimed in claim 1 wherein the reaction is conducted at from about 20° C. to about 100° C.

4. A process as claimed in claim 2 wherein the reaction is conducted at from about 20° C. to about 100° C.

5. A process as claimed in claim 1 wherein the solvent is acetonitrile.

6. A process as claimed in claim 2 wherein the solvent is acetonitrile.

7. A process as claimed in claim 3 wherein the solvent is acetonitrile.